United States Patent
Downer

(10) Patent No.: US 8,968,397 B2
(45) Date of Patent: Mar. 3, 2015

(54) INTRAOCULAR LENS SURGICAL SYSTEM AND METHOD

(71) Applicant: Novartis AG, Fort Worth, TX (US)

(72) Inventor: David A. Downer, Fort Worth, TX (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/069,962

(22) Filed: Nov. 1, 2013

(65) Prior Publication Data

US 2014/0066947 A1    Mar. 6, 2014

Related U.S. Application Data

(63) Continuation of application No. 13/252,548, filed on Oct. 4, 2011.

(51) Int. Cl.
*A61F 2/16* (2006.01)
*A61F 9/00* (2006.01)

(52) U.S. Cl.
CPC ............ *A61F 2/1678* (2013.01); *A61F 9/0017* (2013.01)
USPC ......................................... 623/6.12; 606/107

(58) Field of Classification Search
USPC .......................... 623/6.11, 6.12; 606/107, 166
See application file for complete search history.

(56) References Cited

U.S. PATENT DOCUMENTS

| | | | |
|---|---|---|---|
| 4,681,102 A | 7/1987 | Bartell | |
| 4,919,130 A | 4/1990 | Stoy et al. | |
| 5,275,604 A | 1/1994 | Rheinish et al. | |
| 5,494,484 A | 2/1996 | Feingold | |
| 5,499,987 A | 3/1996 | Feingold | |
| 5,616,148 A | 4/1997 | Eagles et al. | |
| 5,620,450 A | 4/1997 | Eagles et al. | |
| 5,653,715 A | 8/1997 | Reich et al. | |
| 5,947,976 A | 9/1999 | Van Noy et al. | |
| 6,093,193 A | 7/2000 | Makker et al. | |
| 6,143,001 A | 11/2000 | Brown et al. | |
| 6,537,283 B2 | 3/2003 | Van Noy | |
| 2005/0149058 A1* | 7/2005 | Lin et al. | 606/107 |
| 2007/0005135 A1 | 1/2007 | Makker et al. | |
| 2007/0123980 A1* | 5/2007 | Peterson et al. | 623/6.12 |
| 2008/0147081 A1 | 6/2008 | Pynson | |
| 2009/0112223 A1 | 4/2009 | Downer et al. | |
| 2009/0292293 A1 | 11/2009 | Bogaert et al. | |
| 2009/0318933 A1 | 12/2009 | Anderson | |
| 2011/0098716 A1 | 4/2011 | Peterson et al. | |
| 2012/0158007 A1 | 6/2012 | Brown et al. | |

OTHER PUBLICATIONS

PCT International Preliminary Report on Patentability and Written Opinion, PCT/US2012/054413, dated Apr. 8, 2014, 6 pages.

* cited by examiner

*Primary Examiner* — Jocelin Tanner
(74) *Attorney, Agent, or Firm* — Darien Reddick

(57) ABSTRACT

Various systems, apparatuses, and processes may be used for intraocular lens surgery. In particular implementations, a system for intraocular lens surgery may include an intraocular lens insertion cartridge and an intraocular lens interface adapted to engage intraocular lens for advancement through the intraocular lens insertion cartridge. The system may also include a bracket that is detachably attached to the intraocular lens insertion cartridge and that facilitates securing the intraocular lens interface relative to the intraocular lens insertion cartridge.

10 Claims, 3 Drawing Sheets

INTRAOCULAR LENS SURGICAL SYSTEM AND METHOD

CROSS-REFERENCE TO RELATED APPLICATIONS

This Application is a continuation application of prior application Ser. No. 13/252,548, filed Oct. 4, 2011, the entire contents of which is incorporated herein by reference.

BACKGROUND

The present disclosure relates to optical surgery, and more specifically to surgery for replacement of a patient's lens.

The human eye, in simple terms, functions to provide vision by transmitting and refracting light through a clear outer portion called the cornea and focusing the image by way of the lens onto the retina at the back of the eye. The quality of the focused image depends on many factors including the size, shape, and length of the eye, and the shape and transparency of the cornea and lens.

When trauma, age, or disease causes the lens to become less transparent, vision deteriorates because of a reduction in light transmitted to the retina. This deficiency in the eye's lens is medically known as a cataract. The treatment fur this condition is typically surgical removal of the lens and implantation of an artificial lens, often termed an intraocular lens (IOL).

BRIEF SUMMARY

In one general implementation, a system for intraocular lens (IOL) surgery may include an IOL insertion cartridge and an IOL interface adapted to engage an IOL lens for advancement through the IOL insertion cartridge. The system may also include a bracket that is detachably attached to the IOL insertion cartridge and that facilitates securing of the IOL interface relative to the IOL insertion cartridge.

In certain implementations, the bracket may form a cavity between itself and the IOL insertion cartridge for securing at least a portion of the IOL interface. The cavity may, for example, be sized to hold the IOL interface in place by friction between the IOL interface and the bracket and the IOL insertion cartridge. The IOL insertion cartridge may also include protuberances that form part of the cavity.

In particular implementations, the bracket includes a detent that inhibits the IOL interface from being advanced through the cavity during engagement with an IOL insertion tool. Moreover, the detent may be used for storing energy in the IOL interface to aid in removing it from the system.

The bracket may, for example, attach to the IOL insertion cartridge due to a friction fit. In certain implementations, for instance, the bracket may include a truncated V-shaped body with wings that engage the IOL insertion cartridge. Additionally, the truncated portion of the V-shaped body may form part of a cavity for securing the IOL interface.

In another general implementation, a process for using an IOL surgical system may include positionally stabilizing an assembly including an IOL insertion cartridge, an IOL interface, and a detachable bracket and removing the IOL interface from the assembly. The process may also include detaching the bracket from the IOL insertion cartridge.

In an additional general implementation, a process for making an IOL surgical system may include detachably attaching an IOL insertion cartridge to a bracket that facilitates securing of an IOL interface relative to the IOL insertion cartridge and engaging an IOL interface with the bracket.

Various implementations may include one or more features. For example, a system for IOL surgery may allow an IOL interface to be co-located with an IOL insertion cartridge, which assists in preventing the IOL interface, which may often be relatively small, from being lost. As another example, a system may allow an IOL interface to be positioned relative to an IOL insertion cartridge in a stable manner. Thus, grasping the IOL insertion cartridge, which is typically much larger than the IOL interface and, hence, easier to grasp (whether by hand or tool), allows control over the IOL interface. Moreover, because of the typically small size of an IOL interface, manual grasping of it through a surgical glove may be difficult, especially if the glove is wet. Additionally, this eliminates a handling operation, and a separate assembly device is not required. As a further example, an IOL interface may be readily presented for engagement with an IOL insertion tool, which may ease the engagement process.

The details and features of various implementations will be conveyed by the following description, along with the drawings.

DETAILED DESCRIPTION

Figure 1:
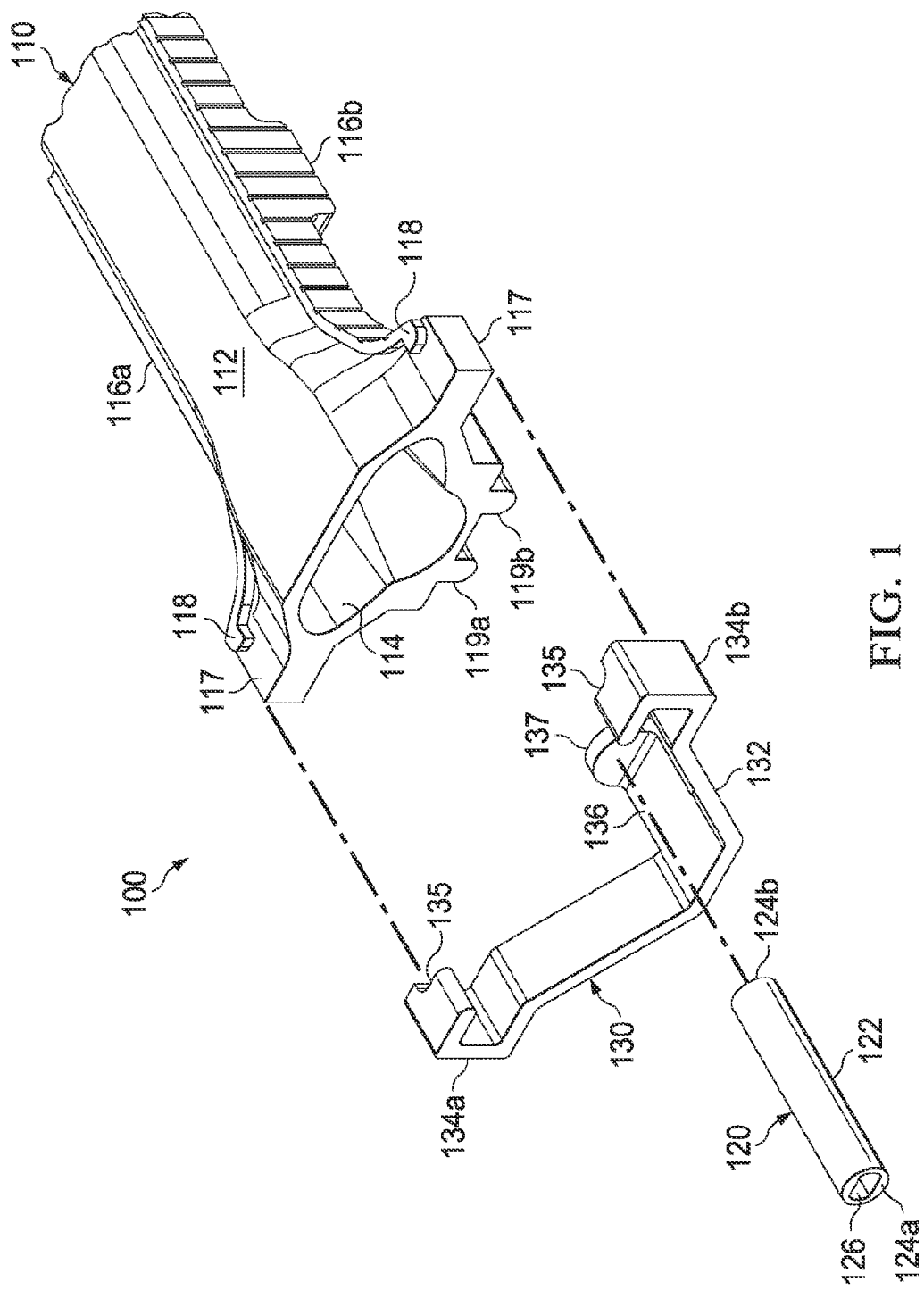
FIG. 1 is an exploded view of an example system for intraocular lens surgery.

FIG. 1 illustrates an example system 100 for intraocular tens (IOL) surgery. System 100 includes an IOL insertion cartridge 110, an IOL interface 120, and a detachable bracket 130.

IOL insertion cartridge 110 facilitates the insertion of an IOL into a patient's eye. IOL insertion cartridge 110 includes a body 112 and a passage 114 through the body. During surgery, a foldable IOL, which may be made of silicone, soft acrylics, hydrogels, or other appropriate materials, is moved through passage 114 in preparation for insertion into the eye.

As shown, passage 114 has an asymmetric bore, which assists in folding an IOL. A common IOL may be approximately 6 mm in diameter, and with haptics can be up to around 13 mm. However, surgical incisions are typically much smaller (e.g., 2 to 3 mm in width). An IOL is therefore typically folded before insertion through the incision. In particular implementations, passage 114 may also taper along its length (e.g., to a circular or elliptical bore) to assist in folding an IOL. Thus, as an IOL is advanced through passage 114, the IOL is folded due to the shape of the passage. At the end of the passage (e.g., the injection point), there is typically a relatively small diameter injection nozzle through which the lens may be advanced into the eye.

IOL insertion cartridge 110 also includes a pair of protuberances 119, which extend from body 112. Protuberances 119 may generally assist in the placing and securing of IOL interface 120. In the illustrated implementation, protuberances 119 are a pair of parallel legs spaced apart from each other sufficiently to allow the IOL interface to be placed between them. Protuberances 119 may therefore assist in placing, aligning, and securing of the IOL interface.

IOL insertion cartridge 110 further includes sides 116a, 116b. Sides 116a, 116b may assist in the grasping (by tool or hand) of IOL insertion cartridge 110, and system 100 accordingly. At one end of IOL insertion cartridge, sides 116a, 116b taper outward to form wings 117, which are used in securing detachable bracket 130 to the IOL insertion cartridge, as discussed in more detail below. Wings 117 include detents 118, which may assist in positioning detachable bracket 130 on wings 117.

In certain implementations, IOL insertion cartridge 110 may be molded as a single piece from any suitable thermoplastic, such as polypropylene. In particular implementations, the thermoplastic may contain a lubricity enhancing agent.

IOL interface 120 is responsible for interfacing with an IOL to advance it through IOL insertion cartridge 110. In this implementation, IOL interface 120 includes a body 122 having a generally cylindrical shape and a first end 124a and a second end 124b. First end 124a includes a port 126 into which an IOL insertion tool may be inserted. IOL interface 120 may, for example, engage with an IOL insertion tool due to a friction fit. Second end 126a may be closed. IOL interface 120 may be made of a commercial injection-molded elastomer, polymer (e.g., polypropylene or styrene) or any other appropriate material. In particular implementations, IOL interface may be approximately 2 to 3 mm in diameter.

Detachable bracket 130 is adapted to detachably attach to IOL insertion cartridge 110 and secure IOL interface 120 relative to the IOL insertion cartridge 110. In this implementation, detachable bracket 130 includes a body 132 having a truncated V-shape. The ends of the V-shape are flattened to provide support surfaces for IOL insertion cartridge 110. Coupled to the ends of the V-shape are wings 134. Wings 134 are spaced apart from each other to receive wings 117 of IOL insertion cartridge 110. Each of wings 134 includes a tab 135. Tabs 135 form cavities into which wings 117 of IOL deliver cartridge fit and are be spaced from the flattened portions of body 132 to provide a fiction fit for wings 117.

Detachable bracket 130 also includes a detent 136 that retards the movement of IOL interface 120 during use. In the illustrated implementation, detent 136 extends from the truncated portion of body 132 and includes a protuberance 137. Protuberance 137 is sized to interact with end 124b of IOL interface 120.

Detachable frame 130 may be composed of plastic (e.g., styrene, polypropylene, or any other commercially available injection-molded polymer), metal (e.g., titanium, stainless steel, or aluminum), or any other appropriate material. In the illustrated implementations, detachable bracket 130 is approximately 3 mm in width (i.e., in the longitudinal direction of body 112) and 1 mm in thickness. However, detachable bracket 130 may be sized. For example, detachable bracket 120 may be sized according to a desired application. Further, detachable bracket 130 may also have other shapes. For example, instead of a truncated V-shape, detachable bracket 130 may have a square or rectangular shape. Thus, detachable bracket 130 may be appropriately sized and configured to work with various IOL cartridge designs.

Figure 2A:
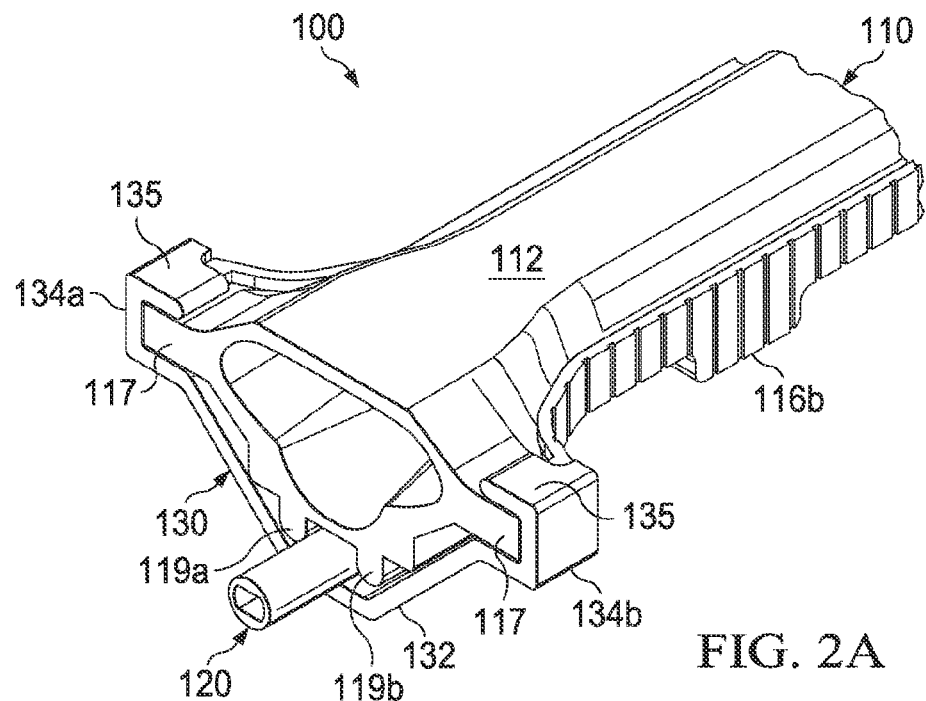
FIGS. 2A-B show perspective views of the system of FIG. 1 in an assembled state.
Figure 2B:
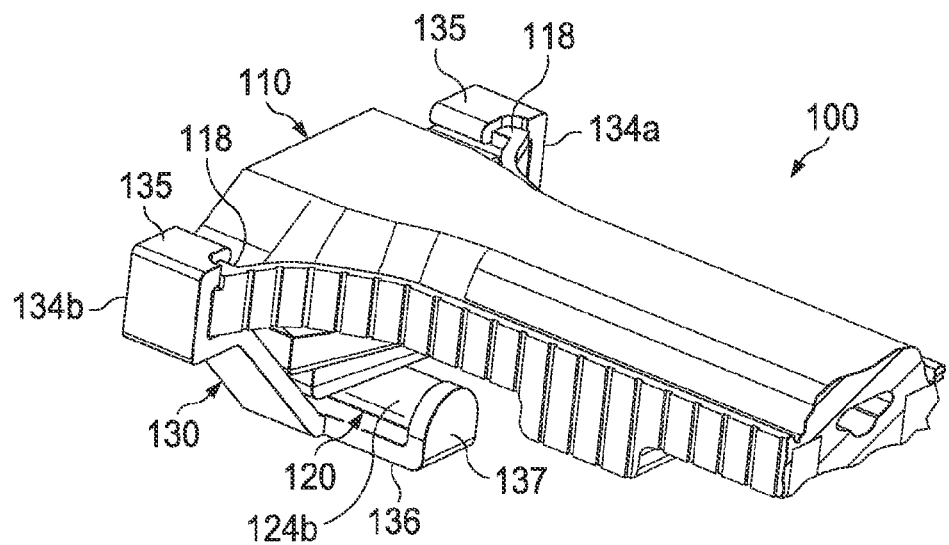

FIGS. 2A-B illustrate system 100 in an assembled state. As best illustrated in FIG. 2A, IOL insertion cartridge 110 has been engaged with detachable bracket 130 by having wings 117 inserted between wings 134 and between the flattened portions of body 132 and tabs 135. Wings 117 may, for example, be held in place due to a friction fit. Additionally, IOL interface 120 has been engaged with system 100 by being captured in a cavity formed between the truncated portion of body 132, protuberances 119, and a portion of body 112. IOL interface 120 may be held in the cavity due to a friction fit.

As best illustrated in FIG. 2B, end 124b of IOL interface 120 is inhibited from moving beyond a particular location along IOL insertion cartridge 110 by protuberance 137 of detent 136. This may prevent IOL interface 120 from sliding through the cavity formed between IOL insertion cartridge 110 and detachable bracket 130, during assembly and/or use. Additionally, tabs 135 may abut detents 118 to prevent detachable bracket 130 from sliding along the longitudinal direction of body 112, which may assist in securely mounting detachable bracket 130 to IOL insertion cartridge 110.

In certain modes of operation, system 100 arrives in an assembled, sterilized state at a surgical site (e.g., hospital). System 100 may then be positionally stabilized (by a tool or by hand), and a tool that is used to advance an IOL through IOL insertion cartridge 100 may be engaged with IOL interface 120. For example, an IOL insertion tool may be inserted into port 126 of IOL interface 120, and a friction fit may be formed between the two components due to the insertion.

An IOL insertion tool may, for example, be a plunger-style system that includes an outer shell and a plunger. The outer shell may have passage therethrough, and the plunger may be adapted to move in the passage, the plunger movements causing the IOL to move. The shell and plunger may, for example, be generally cylindrical in shape. The plunger system may be made of plastic, metal, or any other appropriate material. An example IOL insertion tool is a Monarch® handpiece produced by Alcon Laboratories, Inc., of 6201 South Freeway, Fort Worth, Tex. 76134. However, other types of IOL insertion tools may be used.

While the insertion tool is engaged with IOL interface 120, detent 136 may prevent IOL interface 120 from being advanced out of the cavity. Furthermore, detent 136 may assist in building up energy in IOL interface 120 to assist in removing the IOL interface from system 100.

Once the IOL insertion tool is engaged with IOL interface 120, the IOL interface 120 may be removed from system 100. In particular, the IOL interface 120 may be pulled from the cavity formed between IOL insertion cartridge 110 and detachable bracket 130. The detachable bracket 130 may then be detached from the IOL insertion cartridge. For example, the detachable bracket 130 may be slid relative to the longitudinal axis of the IOL insertion cartridge 110 such that a friction fit between wings 117 and wings 134 is released. Thereafter, the detachable bracket 130 may be discarded. The IOL interface 120 may be used for advancing an IOL through IOL insertion cartridge 110 for insertion into an eye.

System 100 provides a variety of features. For example, system 100 allows IOL interface 120 to be co-located with IOL insertion cartridge 110. Because the IOL interface 120 may be small in size, being co-located with the IOL insertion cartridge 110 may aid in preventing the IOL interface 120 from being lost. As another example, system 100 allows IOL interface 120 to be positioned relative to IOL insertion cartridge 110 in a stable manner. Thus, by grasping IOL insertion cartridge 110, which is typically much larger than IOL interface 120 and, hence, easier to grasp (whether by hand or tool), control may be had over the IOL interface 120.

Further, because the IOL interface 120 may be small in size in some instances, manual grasping of the IOL interface 120, particularly while wearing surgical gloves, may be difficult. This difficulty may be further exasperated if the gloves are wet.

Additionally, co-locating the IOL interface 120 with the IOL insertion cartridge 110 eliminates a handling operation, and a separate assembly device for handling the IOL interface 120 is not required. As a further example, IOL interface 120 may be readily presented for engagement with an IOL insertion tool, which may ease the engagement process. Moreover, the presentation may be quite intuitive, which may ease mental burden. As another example, detachable bracket 130 may be easily detached from IOL insertion cartridge 110 once the IOL interface 120 is removed from system 100. Furthermore, IOL interface 120 is able to be implemented while increasing packaging space a relatively small amount. Moreover, additional packagings are not required.

Although FIGS. 1-2 illustrate one example implementation of an IOL surgical system 100, other implementations may include fewer, additional, and/or a different arrangement of components. In some implementations, for example, IOL insertion cartridge 110 may not include wings 117. Thus, in some implementations, the detachable bracket 130 may engage IOL insertion cartridge 110 by different techniques. For instance, the detachable bracket 130 may engage the sides and/or the top and/or bottom of an IOL insertion cartridge 110.

Additionally, in some instances, the passage 114 may have other configurations. For example, in some implementations, the passage 114 may round, elliptical, or other desired or suitable cross-sectional shapes. Also, in some implementations, the IOL insertion cartridge 110 may not include protuberances 119. Thus, the IOL interface 120 may be secured to system 100 in other manners. For example, a cavity in which the IOL interface 1120 is disposed may be formed between body 112 and body 132. In particular implementations, IOL interface 120 may be engaged primarily with detachable bracket 130.

Figure 3:
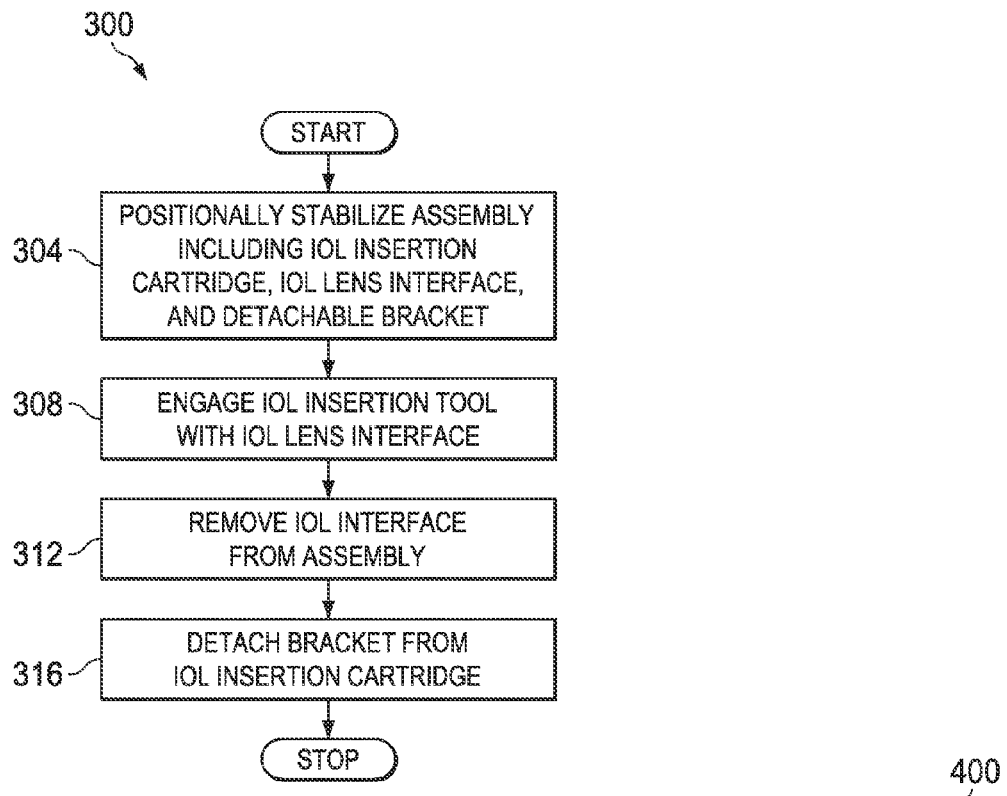
FIG. 3 is a flowchart illustrating an example process for using a system for intraocular lens surgery.

FIG. 3 illustrates an example process 300 for using a system for IOL surgery. For example, process 300 may, for instance, be performed using a system similar to system 100.

Process 300 calls for positionally stabilizing an assembly that includes an IOL insertion cartridge, an IOL interface, and a detachable bracket that holds the IOL interface stable relative to the IOL insertion cartridge (operation 304). For example, in some instances, the assembly may be positionally stabilized by being grasped (e.g., by a tool or hand).

Process 300 also calls for engaging an IOL insertion tool with the IOL interface (operation 308). For example, an IOL insertion tool may be inserted into a port of the IOL interface and a friction fit may be formed between the two components due to the insertion.

Process 300 additionally calls for removing the IOL interface from the assembly (operation 312). For example, the IOL interface may be pulled from a cavity formed between the IOL insertion cartridge and the detachable bracket.

Process 300 further calls for detaching the detachable bracket from the IOL insertion cartridge (operation 316). For example, the detachable bracket may be slid relative to the IOL insertion cartridge such that a friction fit between the two is released. In some instances, the released detachable bracket may be discarded.

Although process 300 illustrates one example of a process for using a system for IOL surgery, other processes for using an IOL surgical system may include fewer, additional, and or a different arrangement of operations. For example, a process may not include detaching the detachable bracket. As a further example, a process may include using the IOL interface to advance an IOL through the IOL insertion cartridge. As an additional example, a process may include advancing the IOL interface against a detent to build energy for removing the IOL interface.

Figure 4:
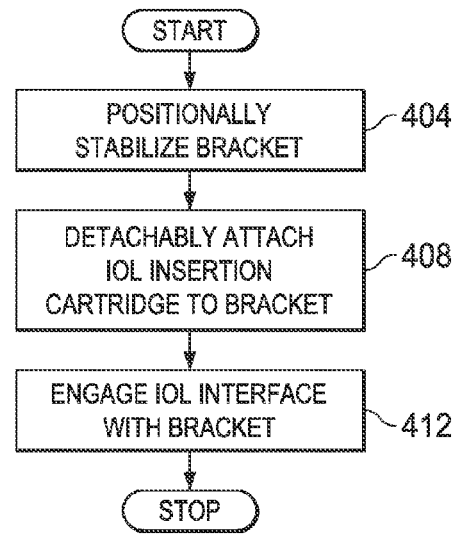
FIG. 4 is a flowchart illustrating an example process for making a system for intraocular lens surgery.

FIG. 4 illustrates an example process 400 for making a system for IOL surgery. In some instances, process 400 may be used to form a system similar to system 100.

Process 404 calls for positionally stabilizing a bracket adapted to engage an IOL interface (operation 404). The bracket may, for example, be stabilized by tool or manually.

Process 400 also calls for detachably attaching an IOL insertion cartridge to the bracket (operation 408). For example, a detachable attachment may be a friction fit.

Process 400 further calls for engaging an IOL interface with the bracket (operation 412). For example, in some instances, an IOL interface may be engaged with a bracket by being inserted into a cavity formed between the bracket and an attached IOL insertion cartridge. The IOL interface may be held in the cavity by a friction fit.

Although process 400 illustrates one example of a process for making a system for IOL surgery, other processes for making an IOL surgical system may include fewer, additional, and/or a different arrangement of operations. In certain implementations, for example, a process may include positionally stabilizing the IOL insertion cartridge and detachably attaching the bracket to the IOL insertion cartridge. Additionally, in some implementations, the IOL interface may be engaged with the bracket before the bracket is engaged with the IOL insertion cartridge. Other operations, such as sterilization or packaging, may also be performed in particular implementations.

The various implementations discussed and mentioned herein have been used for illustrative purposes only. The implementations were chosen and described in order to explain the principles of the disclosure and the practical application and to allow those of ordinary skill in the art to understand the disclosure for various implementations with various modifications as are suited to the particular use contemplated. Thus, the actual physical configuration of components may vary. For example, the mentioned size(s) of components and their illustrated sizing relative to each other may vary based on application. Moreover, the shapes of one or more components may vary depending on application. Thus, the illustrative implementations should not be construed as defining the only physical size, shape, and relationship of components.

The terminology used herein is for the purpose of describing particular implementations only and is not intended to be limiting. As used herein, the singular form "a", "an", and "the" are intended to include the plural forms as well, unless the context clearly indicates otherwise. It will be further understood that the terms "comprises" and/or "comprising," when used in the this specification, specify the presence of stated features, integers, steps, operations, elements, and/or components, but do not preclude the presence or addition of one or more other features, integers, steps, operations, elements, components, and/or groups therefore.

The corresponding structure, materials, acts, and equivalents of all means or steps plus function elements in the claims below are intended to include any structure, material, or act for performing the function in combination with other claimed elements as specifically claimed. The description of the present implementations has been presented for purposes of illustration and description, but is not intended to be exhaustive or limited to the implementations in the form disclosed. Many modifications and variations will be apparent to those of ordinary skill in the art without departing from the scope and spirit of the disclosure.

A number of implementations have been described for an IOL surgical system and method, and several others have been mentioned or suggested. Moreover, those skilled in the art will readily recognize that a variety of additions, deletions, modifications, and substitutions may be made to these implementations while still providing an MIL surgical system and method. Thus, the scope of the protected subject matter should be judged based on the following claims, which may capture one or more concepts of one or more implementations.

The invention claimed is:

1. A system comprising:
an intraocular lens insertion cartridge comprising:
a body;
an enclosed passage extending through the body; and
first wings;
a detachable bracket coupled to the intraocular lens insertion cartridge, the bracket comprising:
second wings; and
tabs formed on the second wings, the tabs defining slots adapted to receive the first wings of the intraocular lens cartridge;
a cavity formed between an exterior surface of the intraocular lens insertion cartridge and the detachable bracket; and
an intraocular lens interface adapted to engage an intraocular lens for advancement through the intraocular lens insertion cartridge, at least a portion of the intraocular lens interface wholly disposed within the cavity, wherein the bracket comprises a detent, wherein the intraocular lens interface is disposed within the cavity between the detent of the bracket and an exterior surface of the intraocular lens insertion cartridge.

2. The system of claim 1, wherein the intraocular lens insertion cartridge comprises protuberances, and wherein the intraocular lens interface is disposed within the cavity between the protuberances.

3. The system of claim 1, wherein the bracket is retained onto the intraocular lens insertion cartridge with a friction fit.

4. A system comprising:
an intraocular lens insertion cartridge comprising:
a body;
an enclosed passage extending through at least a portion of the body; and
protuberances extending from an exterior surface of the portion of the body through which the enclosed passage extends;
a detachable bracket coupled to the intraocular lens insertion cartridge;
a cavity defined between the intraocular lens insertion cartridge and the detachable bracket; and
an intraocular lens interface disposed within the cavity between the protuberances,
wherein the intraocular lens insertion cartridge comprises first wings, wherein the bracket comprises second wings, each of the second wings defining a slot, and wherein each of the first wings is received into one of the slots formed by the second wings, and
wherein the first wings comprise detents, wherein the second wings comprise tabs, and wherein the tabs engage the detents to prevent relative movement of the intraocular lens insertion cartridge and the bracket in a first direction.

5. The system of claim 4, wherein the intraocular lens interface comprises a cylindrical shape.

6. The system of claim 4, wherein the bracket comprises a detent, and wherein the detent extends along the intraocular lens interface disposed within the cavity.

7. The system of claim 6, wherein the bracket comprises a protuberance formed at an end of the detent, the detent is adapted to engage an end of the intraocular lens interface.

8. A system comprising:
an intraocular lens insertion cartridge comprising:
a body;
an enclosed passage extending through the body; and
first wings;
a detachable bracket coupled to the intraocular lens insertion cartridge, the bracket comprising:
second wings; and
tabs formed on the second wings, the tabs defining slots adapted to receive the first wings of the intraocular lens cartridge;
a cavity formed between an exterior surface of the intraocular lens insertion cartridge and the detachable bracket; and
an intraocular lens interface adapted to engage an intraocular lens for advancement through the intraocular lens insertion cartridge, at least a portion of the intraocular lens interface wholly disposed within the cavity, wherein the intraocular lens insertion cartridge comprises protuberances, and wherein the intraocular lens interface is disposed within the cavity between the protuberances, and
wherein the bracket comprises a protuberance formed at an end of a detent, the detent is adapted to engage an end of the intraocular lens interface.

9. A system comprising:
an intraocular lens insertion cartridge comprising:
a body;
an enclosed passage extending through the body; and
first wings;
a detachable bracket coupled to the intraocular lens insertion cartridge, the bracket comprising:
second wings; and
tabs formed on the second wings, the tabs defining slots adapted to receive the first wings of the intraocular lens cartridge;
a cavity formed between an exterior surface of the intraocular lens insertion cartridge and the detachable bracket; and
an intraocular lens interface adapted to engage an intraocular lens for advancement through the intraocular lens insertion cartridge, at least a portion of the intraocular lens interface wholly disposed within the cavity, wherein the intraocular lens interface comprises a port at a first end, the port operable to receive an IOL insertion tool.

10. A system comprising:
an intraocular lens insertion cartridge comprising:
a body;
an enclosed passage extending through the body; and
first wings;
a detachable bracket coupled to the intraocular lens insertion cartridge, the bracket comprising:
second wings; and
tabs formed on the second wings, the tabs defining slots adapted to receive the first wings of the intraocular lens cartridge;
a cavity formed between an exterior surface of the intraocular lens insertion cartridge and the detachable bracket; and
an intraocular lens interface adapted to engage an intraocular lens for advancement through the intraocular lens insertion cartridge, at least a portion of the intraocular lens interface wholly disposed within the cavity, wherein the first wings comprise detents, wherein the second wings comprise tabs, and wherein the detents of the first wings abut tabs of the second wings.

\* \* \* \* \*